United States Patent [19]

Nelson

[11] 4,366,813
[45] Jan. 4, 1983

[54] KNEE BRACE

[76] Inventor: Ronald E. Nelson, 100 S. Main St., Cambridge, Minn. 55008

[21] Appl. No.: 275,931

[22] Filed: Jun. 22, 1981

[51] Int. Cl.³ .............................................. A61F 3/00
[52] U.S. Cl. ........................................ 128/80 C; 2/24
[58] Field of Search .................. 128/80 C, 87 R, 165, 128/DIG. 15; 2/22, 24

[56] References Cited

U.S. PATENT DOCUMENTS

| 325,280 | 9/1885 | Smalbeck et al. |
|---|---|---|
| 332,727 | 12/1885 | McEwen . |
| 363,516 | 5/1887 | Hackey . |
| 605,299 | 6/1898 | Perrottet . |
| 832,613 | 10/1906 | Krieger . |
| 851,950 | 4/1907 | Le Mat . |
| 921,563 | 5/1909 | Quenzer . |
| 929,179 | 7/1909 | Wood . |
| 1,037,441 | 9/1912 | Collis . |
| 1,081,366 | 12/1913 | Collis . |
| 1,084,197 | 1/1914 | Collis . |
| 2,994,332 | 1/1959 | Cullen .................................... 128/80 |
| 3,046,981 | 7/1962 | Biggs, Jr. et al. ................. 128/80 C |
| 3,073,305 | 3/1958 | Biggs, Jr. ............................. 128/166 |
| 3,298,365 | 12/1963 | Lewis ..................................... 128/80 |
| 3,817,244 | 6/1974 | Taylor ............................... 128/80 C |
| 3,945,046 | 3/1976 | Stromgren ........................ 128/80 C |
| 4,116,236 | 9/1978 | Albert ............................... 128/80 C |

Primary Examiner—John D. Yasko
Attorney, Agent, or Firm—Burd, Bartz & Gutenkauf

[57] ABSTRACT

A flexible knee brace for use by athletes or others requiring knee support. The knee brace offers generalized support to the knee joint in addition to specifically providing lateral support to inhibit lateral and rotary movement of the knee, and support for the kneecap to prevent hyperextension and dislocation. A base comprised as a tubular sleeve of elastic material is configured to closely fit around the knee joint and adjacent upper and lower leg portions. A plurality of generally upright forwardly curved lateral pockets are provided on the medial and distal sides of the base. Resilient elongate stays are located in the pockets to provide lateral support. Cross straps are provided, each having a fixed end secured to one side of the base and a free end extendable around the front of the leg in straddling relationship to the kneecap, to the other side of the base. Releasable means fix the free end of each of the cross straps to the side of the base opposite to the fixed end.

19 Claims, 9 Drawing Figures

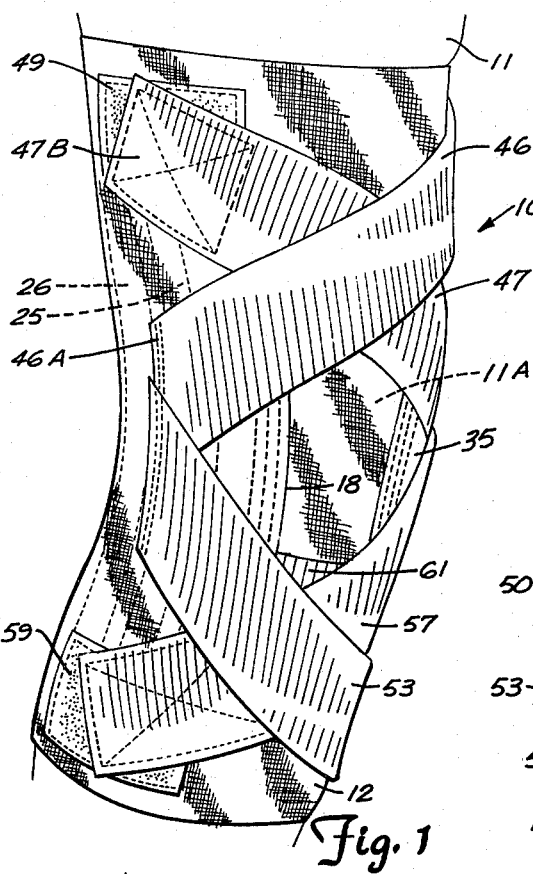
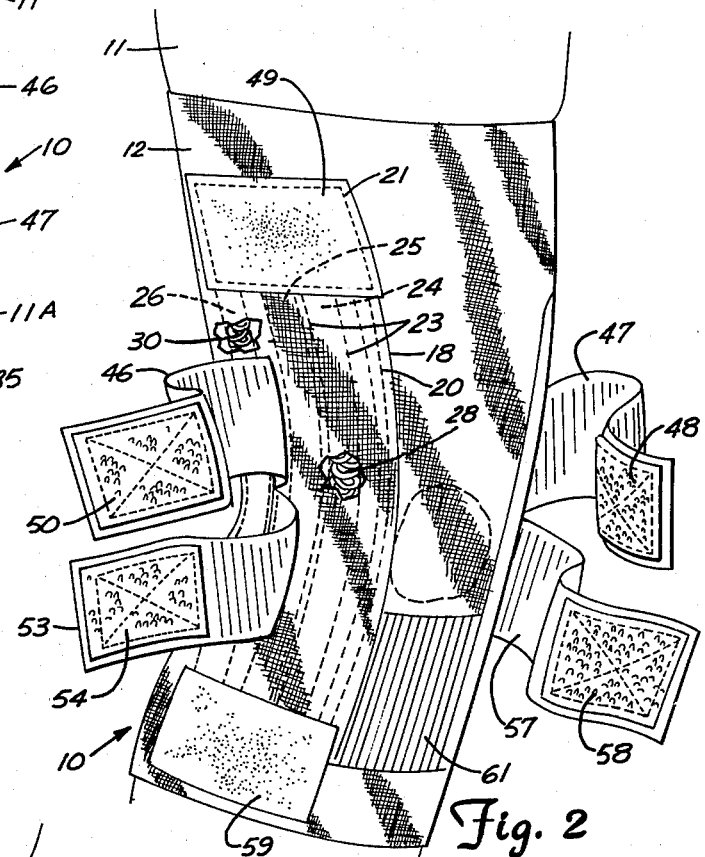
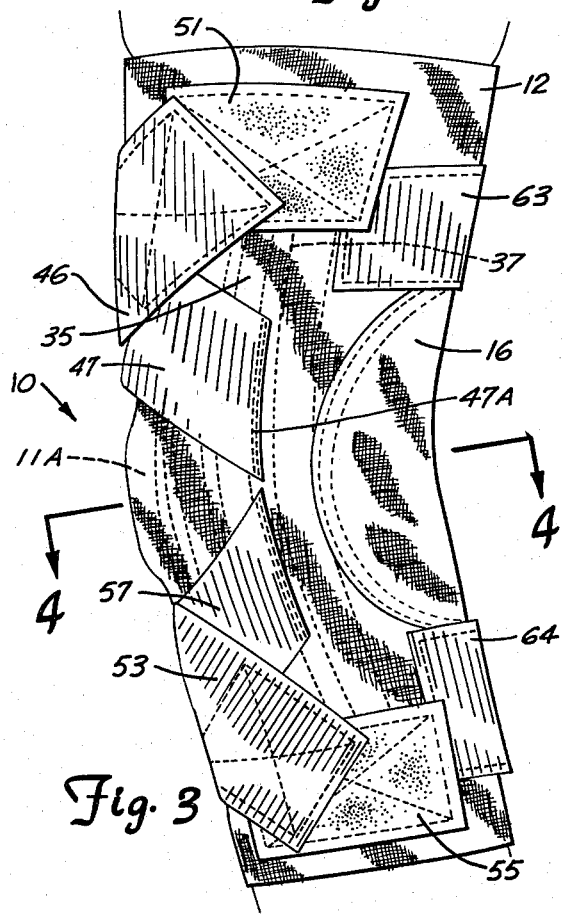
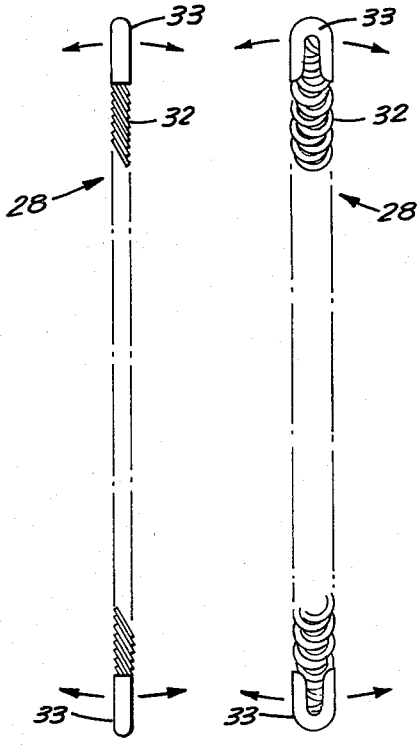

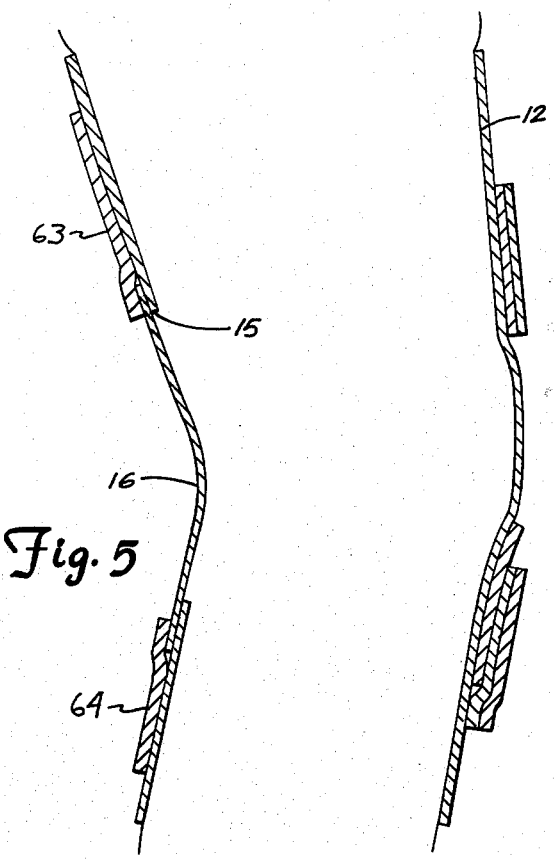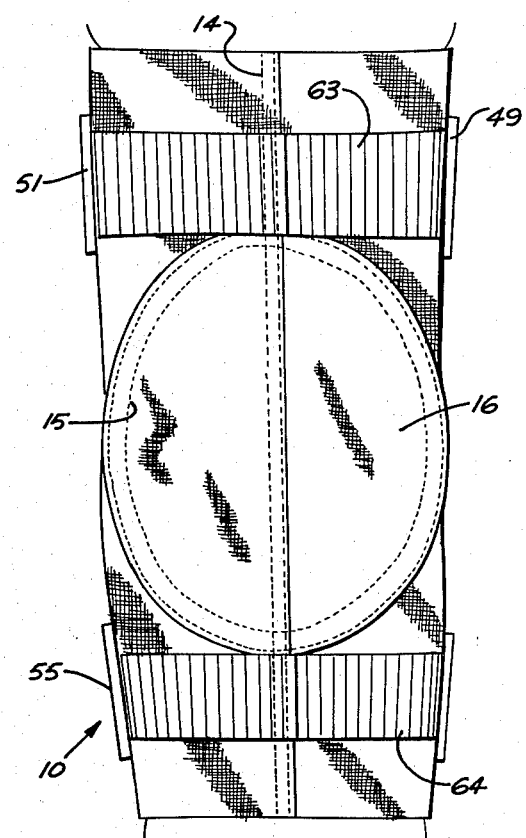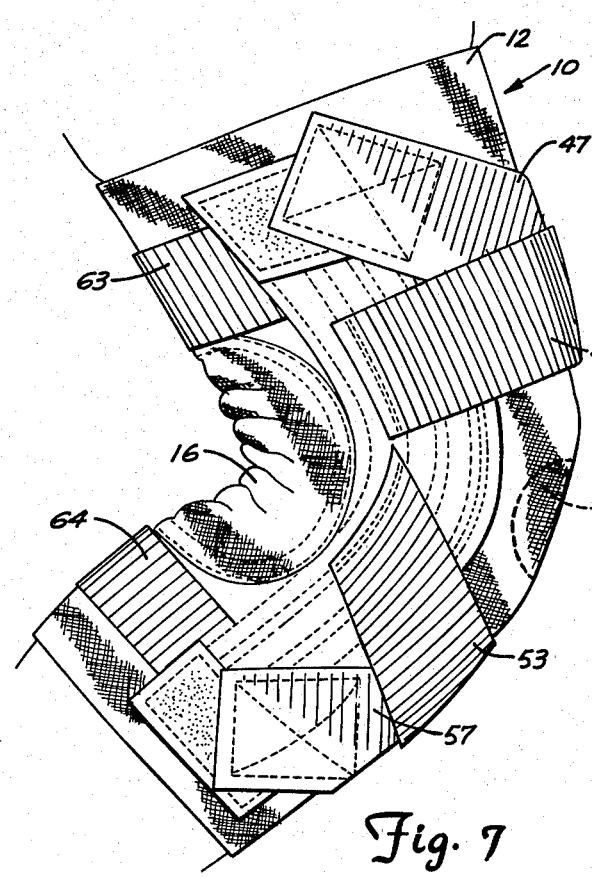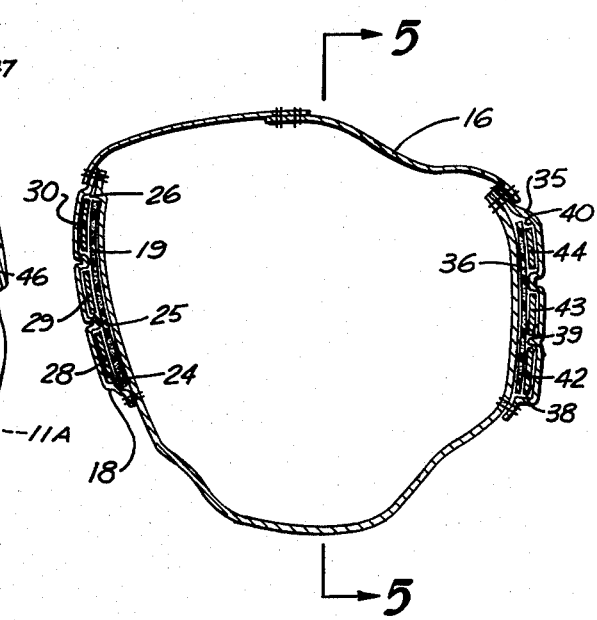

KNEE BRACE

BACKGROUND OF THE INVENTION

The invention pertains to a flexible knee brace or support for athletes to prevent injury to the knee and to protect preexistent injury from aggravation. Potential injury to the knee includes sprain or damage occassioned by lateral movement, rotary movement and hyperextension as well as dislocation. In the prior art, elastic knee pads are in use which provide an elastic sleeve with a padded front portion. These devices offer minimal support and serve primarily to protect the knee in case of a fall. Elastic bandages are sometimes wrapped around the knee joint. These do not give the desired amount of support to the knee and may unduly inhibit flexure of the knee joint particularly by bunching at the back of the knee joint.

The present invention relates to a flexible knee brace for use by athletes or others requiring knee support. The knee brace offers generalized support to the knee joint in addition to specifically providing lateral support to inhibit lateral and rotary movement of the knee, and support for the kneecap to prevent hyperextension and dislocation. The knee brace includes a base comprised as a tubular sleeve of elastic material configured to closely fit around the knee joint and adjacent upper and lower leg portions. A plurality of generally upright forwardly curved lateral pockets are provided on the medial and distal sides of the base. Resilient elongate stays are located in the pockets to provide lateral support. Cross straps are provided, each having a fixed end secured to one side of the base and a free end extendable around the front of the leg in straddling relationship to the kneecap, to the other side of the base. Releasable means fix the free end of each of the cross straps to the rear side of the base opposite to the fixed end. The sleeve has a rear opening in the vicinity of flexure of the knee to permit comfortable bending of the knee. The opening can be covered by a flexible mesh material.

IN THE DRAWINGS

FIG. 1 is a perspective view of a knee brace assembly of tthe invention fitted on the right leg of an athlete or other person requiring knee support and having support straps in engaged positions;

FIG. 2 is a perspective view like that of FIG. 1 showing the support straps of the knee brace in an open or unengaged position;

FIG. 3 is a side elevational view of the knee brace of FIG. 1 showing the side opposite to that shown in FIG. 1;

FIG. 4 is a sectional view of the knee brace of FIG. 3 taken along the line 4—4 thereof;

FIG. 5 is a sectional view of the knee brace shown in FIG. 4 taken along the line 5—5 thereof;

FIG. 6 is a rear elevational view of the knee brace of FIG. 1;

FIG. 7 is a side elevational view of the knee brace as shown in FIG. 1 but with the knee in a flexed orientation;

FIG. 8 is a side elevational view of a flexure stay of a type that can be used in the knee brace of the invention; and FIG. 9 is a front elevational view of the flexure stay of FIG. 8.

DESCRIPTION OF A PREFERRED EMBODIMENT

Referring to the drawings, there is shown in FIGS. 1 through 3 a knee brace indicated generally at 10 worn on a right leg 11 of an athlete or other person requiring knee support. Knee brace 10 includes a tubular base or sleeve 12 formed of a flexible elastic material closely encompassing the knee and adjacent leg portions of leg 11. Sleeve 12 is slightly tapered, being slightly larger at the top than at the bottom for accommodation of the larger upper leg portion. Sleeve 10 can be formed of a single piece of material formed into a tubular shape and sewn up at the back as by the vertical seams 14 shown in FIG. 6. Sleeve 12 has a rear opening 15 in the vicinity of the rear of the knee joint to avoid pinching in that vicinity upon flexure of the knee. Opening 15 can be covered by a light mesh material 16 sewn along the edges of opening 15. Sleeve 12 is fitted in snug relationship at leg 11 to provide generalized support and protection to the knee joint and kneecap indicated at 11A.

Elongate pockets containing resilient stiffening members or stays are located on the medial and distal sides of sleeve 12 to offer lateral support to the knee joint. A flexible distal upright support member 18 is sewn to the distal side of sleeve 12 or the side of sleeve 12 distant from the medium line of the body, extending from near the upper edge of sleeve 12 to a location near the lower edge of sleeve 12. As shown in FIG. 4, a padding or cushion 19 can be disposed between the inner surface of upright support member 18 and the surface of sleeve 12. Distal support member 18 is secured to sleeve 12 as by generally upright seams 20 and generally horizontal seams 21.

A plurality of upright seams 23 are provided through the distal support member 18 to form a plurality of generally upright pockets between distal member 18 and the distal surface of sleeve 12. The padding 19 can be interposed between distal member 18 and sleeve 12. As shown, three generally vertical pockets 24, 25, 26 are formed extending generally the length of distal member 18 and closed at the top and bottom ends, although more or less pockets could be formed as required. Pockets 24, 25, 26 are generally upright in orientation and are slightly forwardly curved in conformance with a slight knee flexure. Two forward pockets 24, 25 are located forward of the flexure axis of the knee. A third rearward pocket 26 is located aft of the flexure axis of the knee.

First, second and third elongate, resilient stiffening members or stays 28, 29, 30 are located respectively in the first, second and third pockets 24, 25, 26. Stays 28, 29, 30 serve to keep sleeve 12 erect to avoid creeping and also serve to impart lateral support to the knee joint. As shown in FIGS. 8 and 9, each stay, for example the stay 28, can be comprised of two helical spring elements interleaved and flattened having an elongate coiled body portion 32 with end caps 33. As so constituted, stay 28 is resiliently flexible about its major axis in all directions as indicated by the arrows in FIGS. 8 and 9. As disposed in pockets 24, 25, 26, stays 28, 29, 30 are orientated in a slightly curved position according to the curvature of the pockets. Stays 28, 29, 30 readily bend upon flexure of the knee but offer some resistance to flexure of the knee and, upon flexure of the knee, offer a bias in a direction to return the knee toward the unflexed position. The stays also offer resistance to twisting of the knee joint.

A flexible medial upright side support member 35 is sewn to the medial side of sleeve 12 opposite and symmetric to the distal support member 18 with a pad 36 interposed between the surface of sleeve 12 and the inner surface of support member 35. In like fashion to distal support member 18, a plurality of seams 37 provide a plurality of medial upright pockets 38, 39, 40 that are forwardly curved in conformance with a slight forward curvature of the knee. Two of the pockets 38, 39 are located forward of the flexure axis of the knee and a third pocket 40 is located aft of the flexure axis of the knee. Third pocket 40 is spaced slightly aft of second pocket 39. A plurality of elongate, resilient stays 42, 43, 44 are located respectively in the pockets, 38, 39, 40 (see FIG. 4). Stays 42-44 can be identical in construction to earlier described stays 28-30. The side support and stay assemblies located on the distal and medial sides of sleeve 12 provide lateral support to the knee joint and inhibit twisting of the knee joint while permitting normal but supported flexure of the knee. As so constituted, brace 10 is symmetrical and can be worn on either knee.

Knee brace 10 is provided with a releasable support strap assembly secured to sleeve 12 to support the knee in the vicinity of the kneecap or patella. A first elastic support strap 46 has one end fixedly secured to a side of the sleeve 12, and a free end extendable around leg 11 in vicinity of the kneecap 11A to the opposite side of sleeve 12. First support strap 46 has one end 46A (See FIG. 1) fixed as by sewing to distal upright support member 18 at a location of spacing between the second distal pocket 25 and the third distal pocket 26. The free end of support strap 46 is extendable generally upwardly and laterally around the leg 11 crossing just above the kneecap 11A. A second support strap 47 has one end 47A (See FIG. 3) fixedly secured to the sleeve 12 at a location opposite to the fixed end 46A of first support strap 46. The fixed end of support strap 47 is secured as by sewing to the medial upright support member at a locaion between the second and third medial pockets 39, 40 approximately midway between the upper and lower edges of sleeve 12. The free end 47B of second support strap 47 is extendable from the fixed end around upwardly and over the kneecap 11A to the opposite side of sleeve 12. Second strap 47 is also linearly elastic. The free end 47B of second strap 47 is provided with releasable fastening means. Releasable fastening means can be of the releasable hook and loop type of fastening means of the variety sold under the trademark Velcro. The free end 47B of second strap 47 has a pad 48 which can carry one portion of the hook and loop type fastening means. Another pad 49 is secured to sleeve 12 at the upper end of distal upright support member 18 and can carry the cooperating portion of the fastening means. Second strap 47 is stretched from its fixed end around the leg 11 just above kneecap 11A and upwardly to the stationary pad 49. The first and second pads 48, 49 are engaged and hold firmly. There is some measure of adjustment permitted as to the point of connection of the pads 48, 49 such that tension in the second strap 47 is adjustable. Likewise, the free end of the first support strap 46 carries a pad 50 that can have the one portion of such hook and loop fastening means. Another pad 51 is secured to the medial side of sleeve 12 toward the upper end of the medial upright support member 35. With sleeve 12 in position on a leg 11, first support strap 46 is stretched from the fixed end 46A around leg 11 above the kneecap and continuing upward to the pad 51. Manual pressure is sufficient to engage the pads 50, 51 where they are held in place. First and second support straps 46, 47 thus crisscross to straddle the upper area encompassing kneecap 11A.

A third linearly elastic support strap 53 has a fixed end secured to the distal side of sleeve 12 intermediate the upper and lower edges thereof and just beneath the point of securement of the fixed end of the first support strap 46. Third strap 53 has a free end extendable about the front of leg 11 and slightly downward from the fixed end to a location on the opposite side of sleeve 12 passing just beneath kneecap 11A. The free end is securable at a location toward the lower medial side of sleeve 12. The free end has a pad 54 which is fastenable to another stationary pad 55 fixed to sleeve 12 at the lower edge of medial upright support member 35.

A fourth strap 57 has one end fixed at a central location on the medial side of sleeve 12 just beneath the location of fixation of the fixed end of second strap 47. Fourth strap 57 has a free end extendable around the front of leg 11 slightly downward to cross diagonally just beneath kneecap 11A and extend to a location on the lower distal side of sleeve 12. Free end of strap 59 carries a pad 58 having a portion of a hook-hoop fastening assembly. Another pad 59 is fastened to the lower edge of upright distal support member 18 and carries a complimentary portion of the hook-loop assembly. With the free end of fourth strap 57 extended around leg 11 just beneath kneecap 11A, pad 58 can be releasably secured to pad 59 with the strap 57 in tension to provide support to the kneecap area. The area encompassed by the respective fastening pads 58, 59 is large enough that the location of pad 58 with respect to pad 59 is adjustable in order that the tension in the fourth strap 57 can be varied.

In the closed position of FIGS. 1, 2 and 7, first and second elastic support straps are in tension and crisscross diagonally in the area above kneecap 11A. Third and fourth elastic support straps are in tension and crisscross diagonally in the area beneath kneecap 11A. Kneecap 11A and surrounding knee joint area are thus well supported against twisting or other adverse movements that might cause injury or dislocation. The tension in the straps is adjustable by adjustment of the locations of the respective pads of each pair. The support straps are readily releasable as shown in FIG. 2 for ease of placement and removal of knee brace 10 from leg 11. The fixed ends of the support straps are fastened between the second and third pockets on the medial and distal upright support members. Rear medial and distal stays 30, 44 located in the third upright pocket on each side of sleeve 12 provide support for these straps when in tension and extended around the leg. These stays serve to distribute the tension pull exerted by the straps over a wider area of sleeve 12 to avoid bunching and a concentration of stress.

Further protection and support for the normally vulnerable area just beneath the kneecap is provided by elastic cross strip 61. Elastic cross strip 61 extends horizontally across the front of leg 11 just beneath the kneecap 11A. One end of elastic cross strip 61 is attached to sleeve 12 adjacent the leading edge of the upright distal support member 18. The opposite end is attached to the sleeve 12 adjacent the leading edge of the upright medial support member 35. Elastic support strip 61 provides support to the region beneath the kneecap and is flexible so as to elongate upon flexure of the knee.

A pair of upper and lower rear horizontal support strips 63, 64 extend across the back of knee brace 10 (See FIG. 6). Upper support strip 63 extends from the trailing edge of upright distal support member 18 behind leg 11 above the opening 15 to the trailing edge of the upright medial support member 35. The ends of the upper rear support strip 63 are secured to sleeve 12 in the location of attachment of the free ends of the support straps 46, 47 in the engaged position. Likewise, lower rear support strip 64 extends around the back of leg 11 between the trailing edges of the upright distal and medial support members beneath opening 15 in the rear of sleeve 12. The respective ends of lower support strip 64 are secured to sleeve 12 near the location of attachment of the free ends of the lower cross support straps 54, 58. Rear horizontal strips 63, 64 serve to impart additional support to the knee and in addition support sleeve 12 against the pull or tug occassioned by the fastened cross support straps 46, 47, 53, 57.

In the use of knee brace 10, sleeve 12 is fitted on a leg 11 as shown in FIG. 2 in covering relationship to the knee joint with the forward horizontal cross strip 61 placed just beneath the kneecap. Upper support straps 46, 47 are fastened in crisscross relationship to the attachment pads in an amount of tension according to the comfort and need of the wearer. In like fashion, lower support straps 53, 57 are fastened in crisscross relationship in the desired amount of tension. Upon flexure of the knee as shown in FIG. 7, the area of sleeve 12 in the vicinity of the kneecap stretches while sleeve 12 still provides generalized support to the knee joint. The flexible stays 28-30, 42-44 flex with the knee joint and provide lateral support. Support straps 46, 47, 53, 57 surround the kneecap and provide lateral support as well as support against dislocation, twisting and other injury. The light mesh material 16 at the rear of the knee joint flexes easily and does not pinch the adjacent leg area.

While there has been shown and described one preferred embodiment of the invention, it will be apparent that changes and deviations may be had from the embodiment shown without departing from the scope and spirit of the invention.

The embodiments of the invention in which an exclusive property or privilege is claimed are defined as follows:

1. A knee brace comprising:
a tubular elastic sleeve positionable in snug covering relationship to a knee and adjacent leg portions;
a first flexible upright support member fixed to a first side of the sleeve, a plurality of first elongate generally vertical pockets formed between the first flexible upright support member and the first side of the sleeve;
first elongate resilient stiffening members located in the first pockets;
a second flexible upright support member fixed to a second side of the sleeve opposite the first support member, a plurality of second elongate generally vertical pockets formed between the second flexible upright support member and the second side of the sleeve;
second elongate resilient stiffening members located in the second pockets;
releasable elastic strap means extendable in tension around the front of the leg between the first upright support member and the second side of the sleeve and between the second upright support member and the first side of the sleeve in the vicinity of the knee for support of the knee joint, said strap means having ends fixed to the first upright support member and the second upright support member forward of one of said resilient members whereby tension pull exerted by the strap means is distributed over a greater portion of the sleeve.

2. The knee brace of claim 1 wherein:
said first and second pockets are formed generally upright and slightly forwardly curved in conformance with a slight knee bend.

3. The knee brace of claim 1 including:
means fixing the first flexible upright support member to the first side of the sleeve comprising parallel generally upright seams sewn between the first flexible upright support member and the first side of the sleeve to form said first pockets; and
means fixing the second flexible support member to the second side of the sleeve comprised as a plurality of parallel generally upright seams sewn between the second flexible upright support member and the second side of the sleeve to form said second pockets.

4. The knee brace of claim 3 wherein:
said first and second pockets are generally upright and slightly forwardly curved in conformance with a slight knee bend.

5. The knee brace of claim 1 wherein:
said releasable elastic strap means includes a first elastic support strap fixed at one end to the first upright support member and having a free end extendable around the front of the leg in the vicinity of the knee, and means to releasably fasten the free end of the first support strap to the second side of the sleeve;
a second elastic support strap fixed at one end to the second upright support member and having a free end extendable around the front of the leg in the vicinity of the knee in crisscross relationship to the first strap, and means to releasably fasten the free end of the second support strap to the first side of the sleeve.

6. The knee brace of claim 1 wherein:
said releasable elastic strap means includes a first elastic support strap having a fixed end fixed to the first upright support member at an intermediate location thereon and having a free end extendable upwardly around the front of the leg in the vicinity of the upper portion of the knee to the second side of the sleeve, means to releasably fasten the free end of the first support strap to the second side of the sleeve located on an upper portion of the second side of the sleeve;
a second elastic support strap having a fixed end fixed to the second upright support member at an intermediate location thereon and having a free end extendable upwardly around the front of the leg in the vicinity of the upper portion of the knee to the first side of the sleeve in crisscross relationship to the first strap, means to releasably fasten the free end of the second support strap to the first side of the sleeve located on an upper portion of the first side of the sleeve;
a third elastic support strap having a fixed end fixed to the first upright support member at an intermediate location thereon and having a free end extendable around the front of the leg in the vicinity of the lower portion of the knee to the second side of the sleeve, means to releasably fasten the free end of the third support strap to the second side of the sleeve located at a lower portion of the second side of the sleeve; and a fourth elastic support strap having a fixed end fixed to the second upright support member at an intermediate location thereon and having a free end extendable around the front of the leg in the vicinity of a lower portion of the knee to the first side of the sleeve in crisscross relationship to the third support strap, means to releasably fasten the free end of the fourth support strap to the first side of the sleeve at a lower portion thereof.

7. The knee brace of claim 6 including:

means fixing the first flexible upright support member to the first side of the sleeve comprising parallel generally upright seams sewn between the first flexible upright support member and the first side of the sleeve to form said first pockets; and means fixing the second flexible support member to the second side of the sleeve comprised as a plurality of parallel generally upright seams sewn between the second flexible upright support member and the second side of the sleeve to form said second pockets.

8. The knee brace of claim 7 wherein:

said first and second pockets are generally upright and slightly forwardly curved in conformance with a slight knee bend.

9. The knee brace of claim 6 wherein:

said sleeve has a rear opening in the vicinity of the locatin of the knee.

10. The knee brace of claim 9 including:

a flexible mesh material covering the rear opening.

11. The knee brace of claim 6 wherein:

two first pockets are located forward of the flexure axis of the knee and one first pocket is located aft of the flexure axis of the knee;

two second pockets being located forward of the flexure axis of the knee and one second pocket being located aft of the flexure axis of the knee.

12. The knee brace of claim 11 including:

a forward horizontal elastic cross strip having ends fastened to said sleeve and extending around the front of the sleeve located to be positioned slightly beneath the kneecap.

13. The knee brace of claim 6 wherein:

the means to releasably fasten the free ends of the first, second, third and fourth support straps comprises a plurality of hook-loop type fastening assemblies.

14. The knee brace of claim 6 including:

a first upper rear horizontal elastic support strip extended across the back of the sleeve toward an upper portion thereof and having ends fixed to the sleeve, and a second lower rear horizontal elastic support strip extended around the back of the sleeve toward a lower portion thereof and having ends fixed to the sleeve.

15. The knee brace of claim 6 wherein:

said sleeve is slightly tappered from top to bottom.

16. A knee brace comprising:

a tubular elastic sleeve positionable in snug covering relationship to a knee and adjacent leg portions;

first upright support means secured to a first side of the sleeve;

second upright support means secured to a secured side of the sleeve opposite the first upright support means;

a first elastic support strap having a fixed end fixed to the first upright support means at an intermediate location thereon and having a free end extendable upwardly around the front of the leg in a vicinity of the upper portion of the knee to the second side of the sleeve, means to releasably fasten the free end of the first support strap to the second side of the sleeve located on an upper portion of the second side of the sleeve;

a second elastic support strap having a fixed end fixed to the second upright support means at an intermediate location thereon and having a free end extendable upwardly around the front of the leg in the vicinity of the upper portion of the knee to the first side of the sleeve, in crisscross relationship to the first strap, means to releasably fasten the free end of the second support strap to the first side of the sleeve located on an upper portion of the sleeve located on an upper portion of the first side of the sleeve;

a third elastic support strap having a fixed end fixed to the first upright support means at an intermediate location thereon and having a free end extendable around the front of the leg in the vicinity of the lower portion of the knee to the second side of the sleeve, means to releasably fasten the free end of the third support strap to the second side of the sleeve located at a lower portion of the second side of the sleeve; and a fourth elastic support strap having a fixed end fixed to the second upright support means at an intermediate location thereon and having a free end extendable around the front of the leg in the vicinity of a lower portion of the knee to the first side of the sleeve in crisscross relationship to the third support strap, means to releasably fasten the free end of the fourth support strap to the first side of the sleeve at a lower portion thereof.

17. The knee brace of claim 16 wherein:

the means to releasably fasten the free ends of the first, second, third and fourth support straps comprises a plurality of hook-loop type fastening assemblies.

18. The knee brace of claim 16 including:

a forward horizontal elastic cross strip having ends fastened to said sleeve and extending around the front of the sleeve located to be positioned slightly beneath the knee joint.

19. The knee brace of claim 16 including:

a forward horizontal elastic cross strip having ends fastened to said sleeve proximate leading edges of the first and second upright support means and extending around the front of the sleeve located to be positioned slightly beneath the knee joint.

* * * * *

UNITED STATES PATENT AND TRADEMARK OFFICE
CERTIFICATE OF CORRECTION

PATENT NO. : 4,366,813
DATED : January 4, 1983
INVENTOR(S) : Ronald E. Nelson

It is certified that error appears in the above-identified patent and that said Letters Patent is hereby corrected as shown below:

Column 7, line 28, "locatin" should be -- location --.

Signed and Sealed this

Twenty-first Day of June 1983

[SEAL]

Attest:

DONALD J. QUIGG

Attesting Officer

Acting Commissioner of Patents and Trademarks